US00PP20094P2

(12) United States Plant Patent
Trucks

(10) Patent No.: US PP20,094 P2
(45) Date of Patent: Jun. 9, 2009

(54) ***SEDUM* PLANT NAMED 'MAESTRO'**

(50) Latin Name: *Sedum (Boreau) hybrid*
Varietal Denomination: Maestro

(76) Inventor: Gary M. Trucks, 1460 Hillandale Rd., Benton Harbor, MI (US) 49022-9761

( * ) Notice: Subject to any disclaimer, the term of this patent is extended or adjusted under 35 U.S.C. 154(b) by 26 days.

(21) Appl. No.: 11/897,858

(22) Filed: Aug. 31, 2007

(51) Int. Cl.
*A01H 5/00* (2006.01)

(52) U.S. Cl. ..... Plt./479
(58) Field of Classification Search ..... Plt./479
See application file for complete search history.

*Primary Examiner*—June Hwu

(57) ABSTRACT

*Sedum* 'Maestro' is a new and distinct cultivar of Stonecrop having bluish-green leaves and stems developing to wine red, with deep pinkish flowers valuable as a landscaping specimen, potted plant, or cut flower.

2 Drawing Sheets

Botanical classification: *Sedum* (Boreau) hybrid.
Variety denomination: 'Maestro'.

BACKGROUND OF THE INVENTION

The present invention relates to the new and distinct cultivar of Stonecrop, botanically known as *Sedum* hybrid, and hereinafter referred to as the cultivar 'Maestro' or the "Plant". The new Plant was discovered in 2002 and developed by the inventor, Gary M. Trucks, in the production fields of a nursery in Benton Harbor, Mich. USA, as a non-induced sport of *Sedum* 'Matrona' (not patented). The plant has been asexually propagated by stem cuttings at the same nursery, and subsequent plants are identical to the original selection.

BRIEF SUMMARY OF THE PLANT

*Sedum* 'Maestro' is unique from all other sedums known to the inventor. Other dark leaf forms of *Sedum,* but no other form has the same bluish leaves developing purplish cast and stems, erect habit and dark pink flowers. 'Maestro' is not as dark purple as *Sedum* 'Black Jack' U.S. Plant Pat. No. 16,736, but is darker purple and more bluish than 'Matrona' (not patented). The plant is more upright and more bluish colored than *Sedum* 'Postman's Pride' U.S. Plant Pat. No. 16,831. The Plant has not been observed in all possible environments. The phenotype may vary slightly with variations in growing conditions such as light intensity and day length, temperature, water availability, and nutrient availability, without, however any variance in genotype. The following are traits of *Sedum* 'Maestro' that distinguish it from all other sedum:

1. Stiff, upright, bluish-green colored glaucous stems developing to a deep wine color.
2. Large, fleshy, thick, bluish green foliage developing to a deep wine colored tinting.
3. Deep pink buds with wine-colored tinting after opening.

BRIEF DESCRIPTIONS OF THE DRAWINGS

The photographs of the new plant demonstrate the unique characteristics and overall appearance of the new cultivar 'Maestro'. The photographs were taken in lightly overcast mid morning light. Colors are as accurate as reasonably possible with color reproductions. Variations in light source, quality and direction may cause the appearance of different colors.

Figure 1:
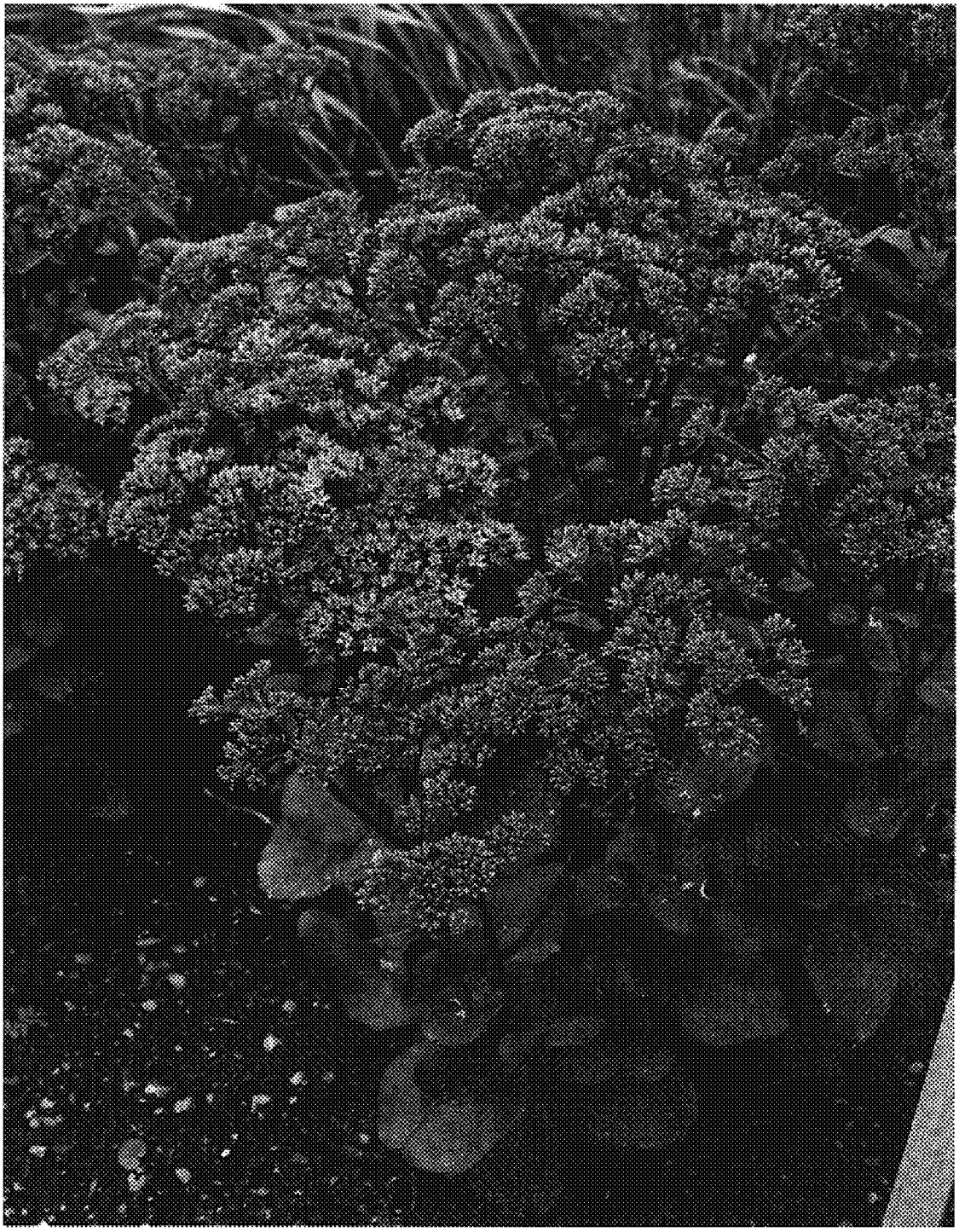

FIG. 1—Shows the plant with habit while in bud and flower.

Figure 2:
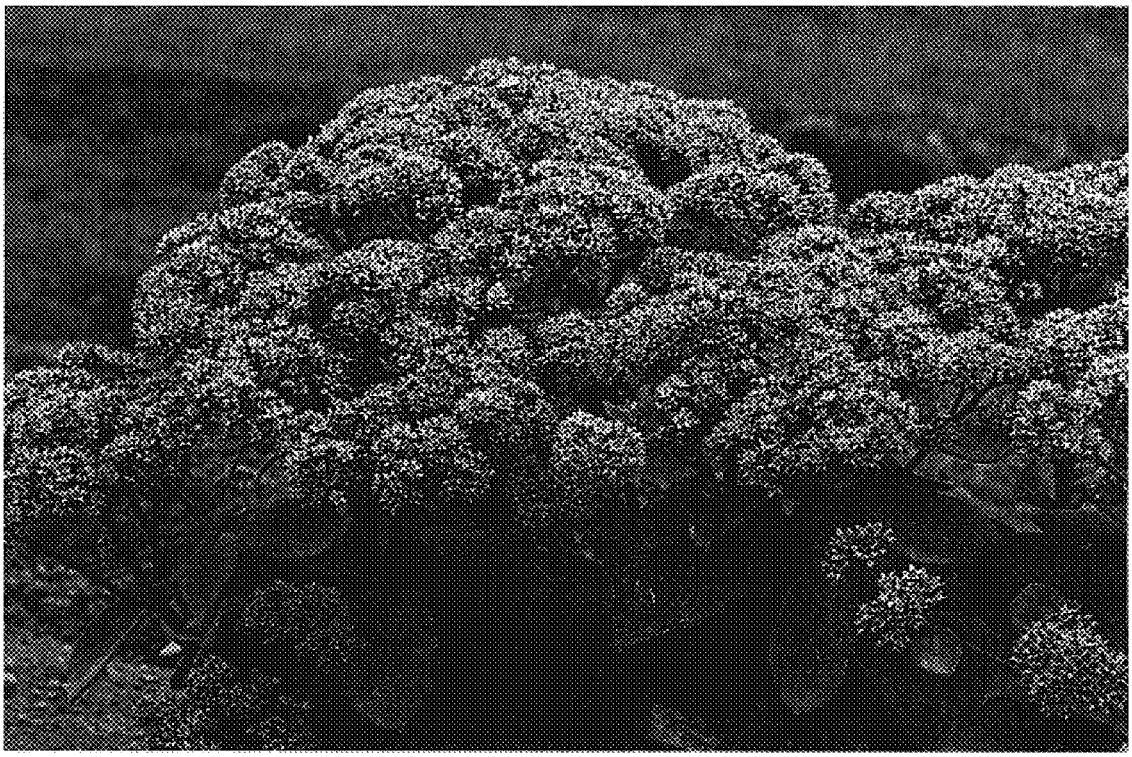

FIG. 2 —Shows the plant in full flower.

DETAILED BOTANICAL DESCRIPTION

The following description uses color references according to the 2001 edition of "The Royal Horticultural Colour Chart", except where general dictionary terms are used. The plant described is grown in a well-drained, loamy sand soil, full-sun trail gardens of a nursery in Benton Harbor, Mich. United States of America, with supplemental fertilization and irrigation. Plants used in this observation have been in the ground two years from cuttings.

Botanical classification: Family — Crassulaccae, *Sedum* (Boreau) hybrid 'Maestro'.
Parentage: *Sedum* 'Matrona' (not patented) uninduced sport.
Propagation: Asexual by cuttings; approximately 14 to 18 days to initiate roots.
Growth rate: Moderate to fast;
Finishing time: About three months from cuttings to fill a two-liter container.
Root description: Tuberous, coarse.
Plant habit and form: Erect stems 1.5 to 2.0 cm in diameter, producing plants between 50 cm and 65 cm tall, 55 cm to 60 cm wide, with alternate leaves.
Internode length: About 2 cm in lower section of the stems and 3 to 4 cm in upper section. Leaves: Glabrous and glaucous on both surfaces; without petioles; broad oval with obtuse apex and rounded based; 9 to 11 cm long by 7.5 to 8.5 cm wide and about 4 mm thick, decreasing in size on the stem with last leaves before the panicle about 4.5 cm long 2.5 cm wide; with few small teeth;
Leaf color shortly after emerging: RHS 143B on both surfaces.
Leaf color four weeks prior to flowering: Top surface more gray than RHS 122B and more blue than RHS 189B; lower surface closest to RHS 133B.

Leaf color at flowering: Top surface RHS N138A stippled with RHS 187A; lower surface closest to RHS 191A;

Petiole: Leaves sessile;

Venation: One large central, same color and tinting as nearby tissue on the lower surface and stippled more heavily than surrounding leaf with RHS 187A on the upper surface; Stem: round, smooth, glaucous, stiff, upright; 10 to 12 mm wide and 26 to 32 cm tall from ground to branching of peduncle; color at flowering between RHS 187B and RHS 187C with a glaucous coating color four weeks prior to flowering RHS 186D; shortly after elongation RHS.

Peduncle: Smooth, glaucous; 9 to 10 cm long and about 10 mm in diameter near base; forming heavily branched umbel 16 to 20 cm across on top; about RHS N 138B with stippling of RHS 183C and glaucous bloom.

Pedicel: Smooth, glaucous; 2 to 4 mm long, about one mm in diameter, RHS N 138B with stippling of RHS 183C and glaucous bloom;

Buds: 6 mm long, 3 mm wide, acute apex RHS 196D stippled with RHS 64A with more concentrated stippling toward apex to nearly solid RHS 64A; Flowers in compact compound corymb; starting in late August and lasting for four weeks through September, approximately 1000 to 1200 per stem; about 10 cm in diameter and 5 cm deep.

Fragrance, None detected;

Petals: Five, with acute apex; 5 mm long, 3 mm wide, RHS 61A to 61B at apex and RHS 69A at base.

Sepals: Five, about 2 mm long and 1 mm wide, with acute apex and; closest to RHS N138A with a light tinting of RHS 187 B;

Style: Five 4 mm long, swollen in center to nearly 2 mm, proximal closest to RHS 62C, distal between RHS 61A to 61B;

Androecium Ten stamens, Filaments 3 to 4 mm long. RHS N155B; Anthers oblong, less than one mm in the longer dimension, darker than RHS N187 A prior to dehiscing, Pollen: Minute; closest to RHS 14B;

Fruit: Minute, about 1 mm in diameter, closest to RHS 200A.

The Plant performs best with light to no fertilization in soils with good drainage, but the plant is resistant to drought and heat, as well as cold tolerance to at least USDA Zone 3. The plant is much less prone to leaf burn or scorch that tends to affect 'Black Jack', but is not known to be resistant to any pests or diseases that commonly affect *Sedum.*

It is claimed:

1. I claim the new and distinct variety of Stonecrop plant, *Sedum* 'Maestro', essentially as herein described and illustrated, having distinguishing characteristics of bluish-green leaves and stems developing to wine red, with deep pinkish flowers valuable as a landscaping specimen, potted plant, or cut flower.

* * * * *